ns | | | |
| [54] | AMINO-ALCOHOL DERIVATIVES |
| [75] | Inventors: Hiroshi Takizawa; Yoshimasa Oiji; Kazuhiro Kubo, all of Shizuoka, Japan |
| [73] | Assignee: Kyowa Hakko Kogyo Co., Ltd., Tokyo, Japan |
| [21] | Appl. No.: 131,490 |
| [22] | Filed: Mar. 18, 1980 |
| [30] | Foreign Application Priority Data |

Mar. 20, 1979 [JP] Japan ................... 54-31750

[51] Int. Cl.$^3$ ........................................... C07D 317/44
[52] U.S. Cl. .............................. 549/366; 260/465 E; 549/467; 560/37; 564/221; 564/348
[58] Field of Search ...................... 260/340.3; 549/366
[56] References Cited

FOREIGN PATENT DOCUMENTS 1245148 9/1971 United Kingdom .
1247370 9/1971 United Kingdom .
1266058 3/1972 United Kingdom .
1493006 11/1977 United Kingdom .
1529972 10/1978 United Kingdom .
1541932 3/1979 United Kingdom .

OTHER PUBLICATIONS

Chem. Abstracts 90(23):186871w.
Chem. Abstracts 92(15):128716e.
Chem. Abstracts 94(13):103390x.
Chem. Abstracts 94(15):121503r.

Primary Examiner—Ethel G. Love
Attorney, Agent, or Firm—Fitzpatrick, Cella, Harper & Scinto

[57] ABSTRACT

New amino-alcohol derivatives and processes for production thereof are disclosed. These compounds exhibit $\alpha$ and $\beta$-adrenergic receptor blocking activity or they act to increase the flow of blood of certain organs.

13 Claims, No Drawings

AMINO-ALCOHOL DERIVATIVES

BACKGROUND OF THE INVENTION

1. Field of the Invention

The present invention relates to new amino-alcohol derivatives having α- and β-adrenergic receptor blocking activity or activity of increasing the blood flow of certain organs and processes for the production thereof.

2. Description of the Prior Art

In anti-hypertensive therapy, it is known to use peripheral vasodilators which act to increase the blood flow of certain organs by relaxing arterial smooth muscles to decrease peripheral resistance and blood pressure. [N. Kaplan, Clinical Hypertension 125 (1973)]. For example, as described in the Merck Index (Ninth Edition) nylidrin (4-hydroxy-α-[1[(1-methyl-3-phenylpropyl)amino]ethyl]benzene methanol)

$$HO-C_6H_4-CH(OH)-CH(CH_3)-NH-CH(CH_3)-CH_2CH_2-C_6H_5$$

is known as a peripheral vasodilator.

It is also known that α-adrenergic receptor blocking drugs promote vasodilation by inhibiting the stimulation of α-receptor sites on vascular smooth muscle or myocardial muscle membrane, which produce arteriolar or venular constriction. Compounds which exhibit α-adrenergic receptor blocking activity include phenoxybenzamine (N-(2-chloroethyl)-N-(1-methyl)-2-phenoxyethyl)benzenemethanamine) and phentolamine (3-[[4,5-dihydro-1H-imidazol-2-yl)methyl] (4-methylphenyl)amino] phenol). [J. Laragh, Hypertension Manual 908 (1973)]. The structure of phenoxybenzamine is shown below.

$$C_6H_5-CH_2-N(CH_2CH_2Cl)-CH(CH_3)-CH_2-OC_6H_5$$

In addition, the antihypertensive effects of β-adrenergic blocking-agents are known to include decrease in cardiac rate and in myocardial contractibility notwithstanding their mild promotion of vasoconstruction. [Frohlich, The Use of Beta-Adrenergic Blockade on Hypertension, Hypertension: Mechanisms and Management 333 (G. Oresti et al ed. 1973)]. As described in the Merck Index (Ninth Edition), β-adrenergic blocking drugs include propanolol (l(isopropylamino)-3-(1-naphthyloxy)-2-propanol) depicted below.

$$\text{Naphthyl-OCH}_2\text{CHCH}_2\text{NHCH}(CH_3)_2 \text{ with OH on central C}$$

While the above compounds exhibit good pharmacological activity, compounds useful to treat cardiovascular disease and the like are always in demand. To this end, the inventors have discovered new compounds which exhibit good pharmacological activity.

SUMMARY OF THE INVENTION

In accordance with the present invention, new amino-alcohol derivatives and their pharmaceutically acceptable acid addition salts are produced having the general formula (I):

$$R_4-CH(OH)-CH(R_3)-NH-CH(R_2)-R_1 \quad (I)$$

wherein $R_1$ represents

[methylenedioxyphenyl groups], $$-CH_2-N(CH_2-C_6H_5)-CH_3-CH-CH_2-O-C_6H_5$$

$$-CH_2-CH_2-C_6H_5 \text{ or } -CH_2-O-C_6H_4-OCH_3,$$

$R_2$ and $R_3$, which may be the same or different, each represent a hydrogen atom or a methyl group and $R_4$ represents a substituted phenyl group, a substituted phenoxymethyl group, a substituted heterocyclyl group or a substituted heterocyclyloxymethyl group. The invention also pertains to various processes for the production of the above compounds.

The compounds of the present invention have α and β-adrenergic receptor blocking activity or they act to increase the flow of blood of certain organs. Accordingly, these compounds are useful as medicaments for cardiovascular diseases such as hypertension, angina pectoris and cerebrovascular diseases and may be used in various pharmaceutical forms of administration.

DESCRIPTION OF THE INVENTION

The novel amino-alcohol derivatives of the present invention are represented by the following general formula (I):

$$R_4-CH(OH)-CH(R_3)-NH-CH(R_2)-R_1 \quad (I)$$

wherein $R_1$ represents (hereinafter referred to as

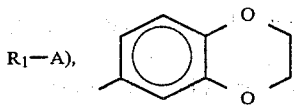

$R_1$—A), (hereinafter referred to as $R_1$-B),

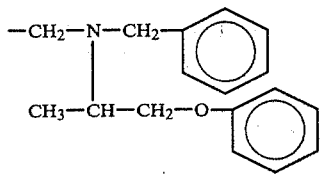

(hereinafter referred to as $R_1$-D),

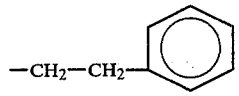

(hereinafter referred to as $R_1$-E) or

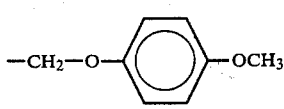

(hereinafter referred to as $R_1$-G), $R_2$ and $R_3$ may be the same or different and represent a hydrogen atom or a methyl group, and $R_4$ represents a substituted phenyl group, a substituted phenoxymethyl group, a substituted heterocyclyl group or a substituted heterocyclyloxymethyl group.

Encompassed within the composition of matter aspect of the invention are the pharmaceutically acceptable acid addition salts of the foregoing compounds.

The substituted phenyl group represented by $R_4$ has from 1 to 3 substituents at the benzene ring. By way of example, the substituent can be an alkylacyl group, an acylamide group, an alkoxy group, an alkoxycarbonyl group, an alkoxycarbonylmethyl group (where the alkyl moiety in each of these substituents has from 1 to 4 carbon atoms), a cyano group, a carbamoylmethyl group, a carbamoyl group, a hydroxy group, a carboxymethyl group, a hydrazinocarbonylmethyl group or a halogen atom.

The substituent in the substituted phenoxymethyl group, the substituted heterocyclyl group or the substituted heterocyclyloxymethyl group represented by $R_4$ can be any of those suitable as substituents for the substituted phenyl group, as illustrated above. The number of substituents at the benzene or heterocyclyl ring for these groups is also from 1 to 3.

The acid addition salts of the present invention include inorganic acid addition salts such as hydrochloride, sulfate, hydrobromide, phosphate and the like, and organic acid addition salts such as acetate, maleate, fumarate, tartrate, citrate, oxalate, benzoate and the like.

The compounds of the present invention can be produced by the following methods.

Method 1

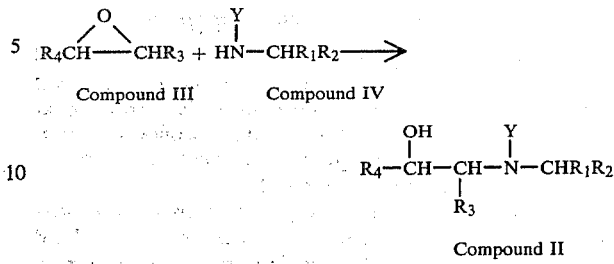

Compound II wherein $R_1$, $R_2$, $R_3$ and $R_4$ have the same meaning as defined before and Y represents a hydrogen atom or an amino protecting group. When Y in Compound II represents a hydrogen atom, Compound II is a compound of the present invention. When Y in Compound II represents an amino protecting group, a compound of the invention can be obtained by eliminating the amino protecting group in a conventional manner.

The reaction is carried out by reacting under reflux an epoxy compound represented by Compound II with an equimolar amount or above, generally one to two moles, of an amine compound represented by Compound IV per one mole of the epoxy compound in an appropriate organic solvent.

After completion of the reaction, the reaction mixture is concentrated under reduced pressure. The resulting residue is then purified by silicagel column chromatography using an organic solvent such as methanol, a recrystallization method using an organic solvent or by other suitable methods to obtain the desired compound in crystalline form or as an oily free base.

Suitable reaction solvents for this reaction include ethanol, methanol, benzene, toluene, chloroform, acrylonitrile and the like. Depending on the amine used as the starting material, however, the reaction may be carried out without solvent (where the amine functions as the solvent) or in solvents other than the above.

The reaction of the present invention is generally carried out at the boiling point of the solvent used, typically at 0°–100° C. The reaction is usually completed in 1–2 hours at a reflux temperature.

When Y in Compound II represents an amino protecting group, e.g., a benzyl group, the desired compound is produced by adding palladium-carbon to the reaction solution and hydrogenolyzing Compound II at room temperature and at atmospheric pressure in a stream of hydrogen. After completion of the reaction, the palladium-carbon is filtered off from the solution. The resulting filtrate is then concentrated under reduced pressure and extracted with ether to obtain the desired compound. Purification and isolation can be carried out in a conventional manner. If in the form of an oil, the compound is dissolved in either or the like, and hydrogen chloride gas is bubbled thereinto to obtain the desired compound as the crystalline hydrochloride. When a by-product is produced in the reaction solution, to overcome the occasional difficulty experienced in separating the desired compound from the reaction solution, silicagel column chromatography is used, which provides ready separation.

The epoxy compound used is readily obtained in a conventional manner. For example, the epoxy compound typically can be obtained by reacting epi-halohydrin with a phenol derivative corresponding to the desired epoxy compound in the presence of a base. Suitable epoxy compounds including those which are used in the Examples which follow are illustrated in Table 1, where Me in the structural formulae represents a methyl group. Except for Compound EP-11 which is described in Reference Example 1 these epoxy compounds are known compounds.

TABLE 1

Epoxy Compounds

| Compound number | Structural formula | Reference |
|---|---|---|
| EP-1 | (structure with Me) | Zh. Org. Khim 465 (1971) |
| EP-2 | (structure) | J. Med. Chem. Vol. 14, 511 (1971) |
| EP-3 | (structure with CN) | Ger. Pat. 1,493,490 (1972) |
| EP-4 | (structure) | J. Med. Chem. Vol. 19, 399 (1976) |
| EP-5 | (structure) | |
| EP-6 | (structure) | Arzneim-Forsch 275 (1973) |
| EP-7 | (structure) | J. Med. Chem. Vol. 11, 1,009 (1968) |
| EP-8 | (structure with $H_2N$) | U.S. Pat. No. 3,663,607 |
| EP-9 | (structure with $CO_2Me$) | Ger. Offen. 2,048,838 |
| EP-10 | (structure with $NH_2$) | Ger. Offen. 2,106,509 (1971) |
| EP-11 | (structure) | Reference Example 1 |
| EP-12 | (structure with $H_2N$) | |

TABLE 1-continued

Epoxy Compounds

| Compound number | Structural formula | Reference |
|---|---|---|
| EP-13 | (structure) | Ger. Offen. 1,948,144 (1970) |

The amine to be used can be readily obtained in a conventional manner. Suitable amines including those which are used in the Examples which follow are shown below. References disclosing these amines are also indicated. In the following structural formulae, Me represents a methyl group, Et represents an ethyl group and Bz represents a benzyl group.

TABLE 2

Examples of Amines

| Amine number | Structural formula | Reference |
|---|---|---|
| AM-1 | (structure with $H_2N$) | Belgian Patent No. 613,213 (1962) |
| AM-2 | (structure with BzN, H) | Arm. Khim. Zh. Vol. 21,509 (1968) |
| AM-3 | (structure with $H_2N$, Me) | J. Med. Pharm. Chem. Vol. 3,167 (1961) |
| AM-4 | (structure with BzN, H, Me) | Japanese published Examined Patent Application No. 43341/73 |
| AM-5 | (structure with $H_2N$, Me, OMe) | U.K. Patent No. 832,286 (1960) |
| AM-6 | (structure with BzN, H, Me, OMe) | (Reference Example 2) |
| AM-7 | (structure with $H_2N$, Me) | (Reference Example 3) |
| AM-8 | (structure with $H_2N$) | French Patent No. 1,476,752 (1967) |

With the exception of Compound AM-7, the amines mentioned above are known compounds. The preparation of these amines are schematically illustrated by the flow sheet which follows. The indicated references in Table 2 above describe the preparation procedure in more detail, and persons skilled in the art can readily prepare these amine compounds.
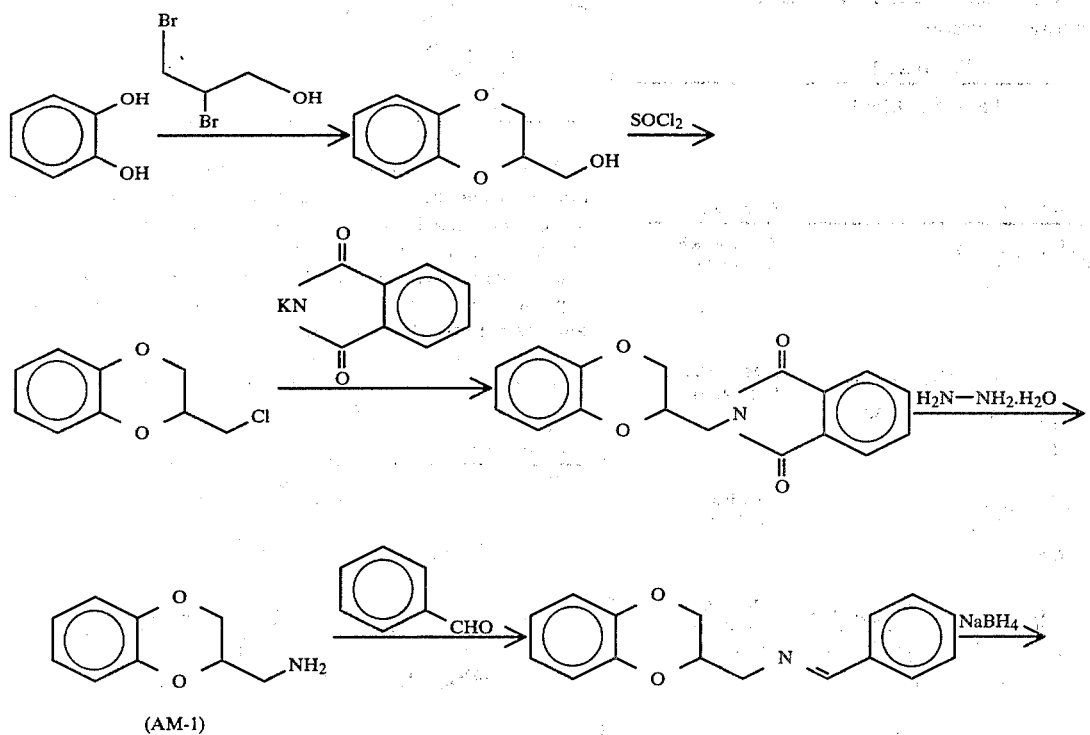
(AM-1)
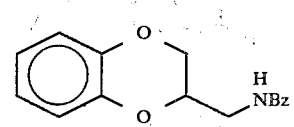
(AM-2)
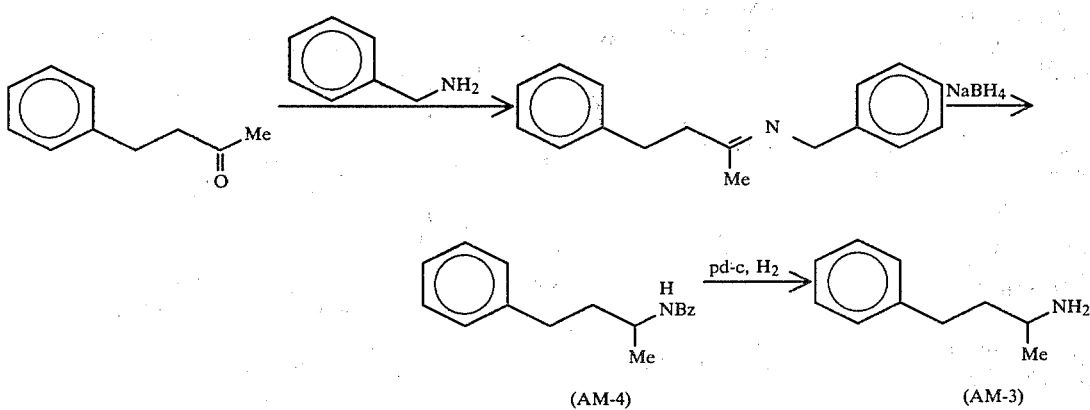
(AM-4)    (AM-3)
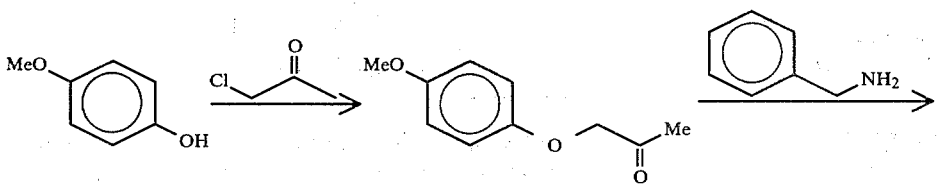

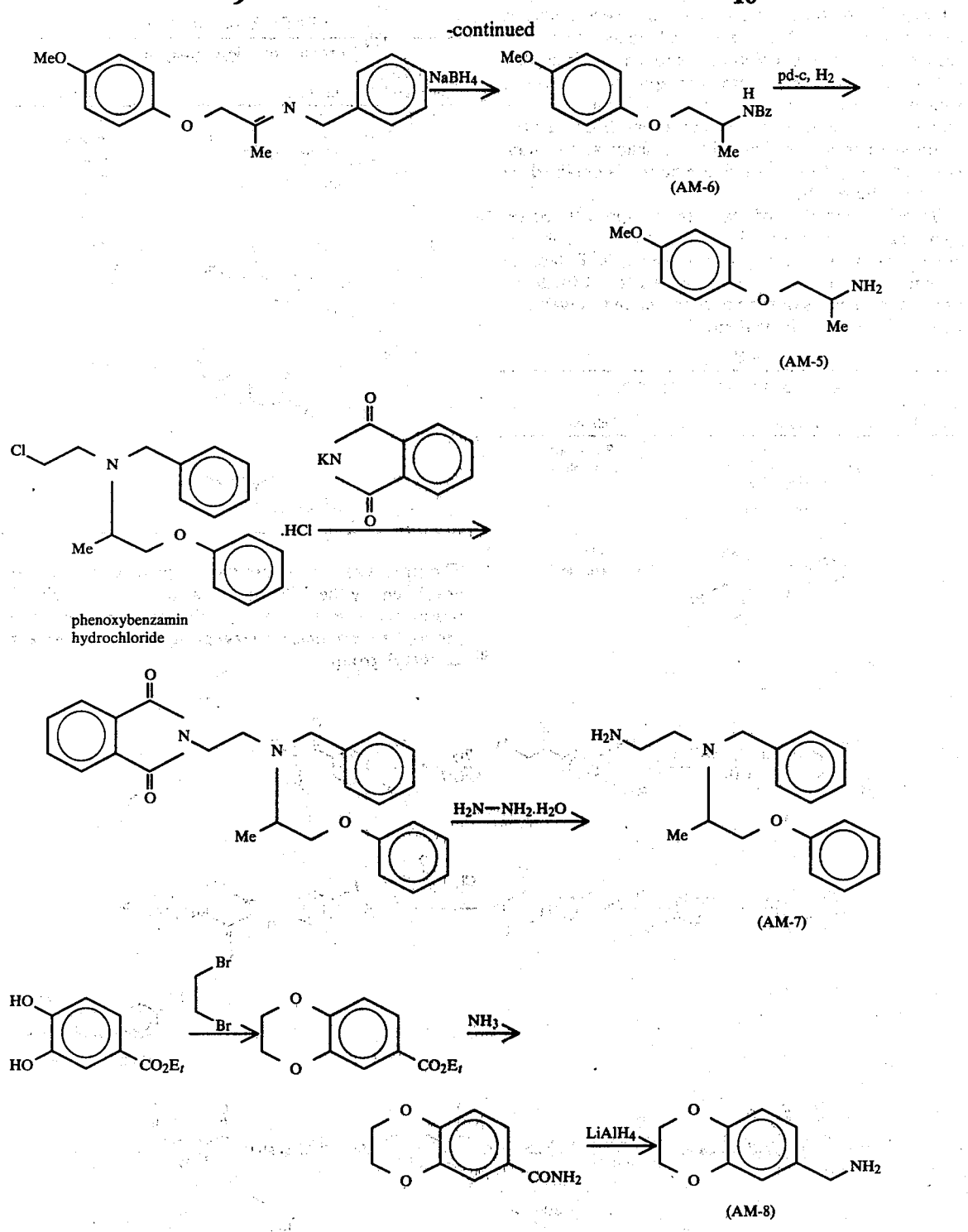
The compounds of the invention, e.g. Compounds 8, 9, 10, 21, etc. as will be discussed hereinafter, can also be obtained by the following methods.
Method 2 wherein $R_1$, $R_2$, $R_3$, $R_4$ and Y have the same meaning as defined before and X represents a halogen atom. The reaction of Compound V with Compound IV is carried out at the reflux temperature in an appropriate solvent, e.g. methylethylketone, acetonitrile and the like. The reaction is generally completed in several hours. To the reaction solution are then added ethanol and sodium borohydride and the desired compound is obtained by reducing the reactant.

Specific examples of halogen compounds corresponding to Compound V are set forth in Table 3. Where the halogen compound is novel, the Reference Example identified has been provided to set forth the physical properties of the novel compound as well as a process for the synthesis thereof.

TABLE 3
Examples of Halogen Compounds

| Compound number | Structural formula | Reference |
|---|---|---|
| X-1 | 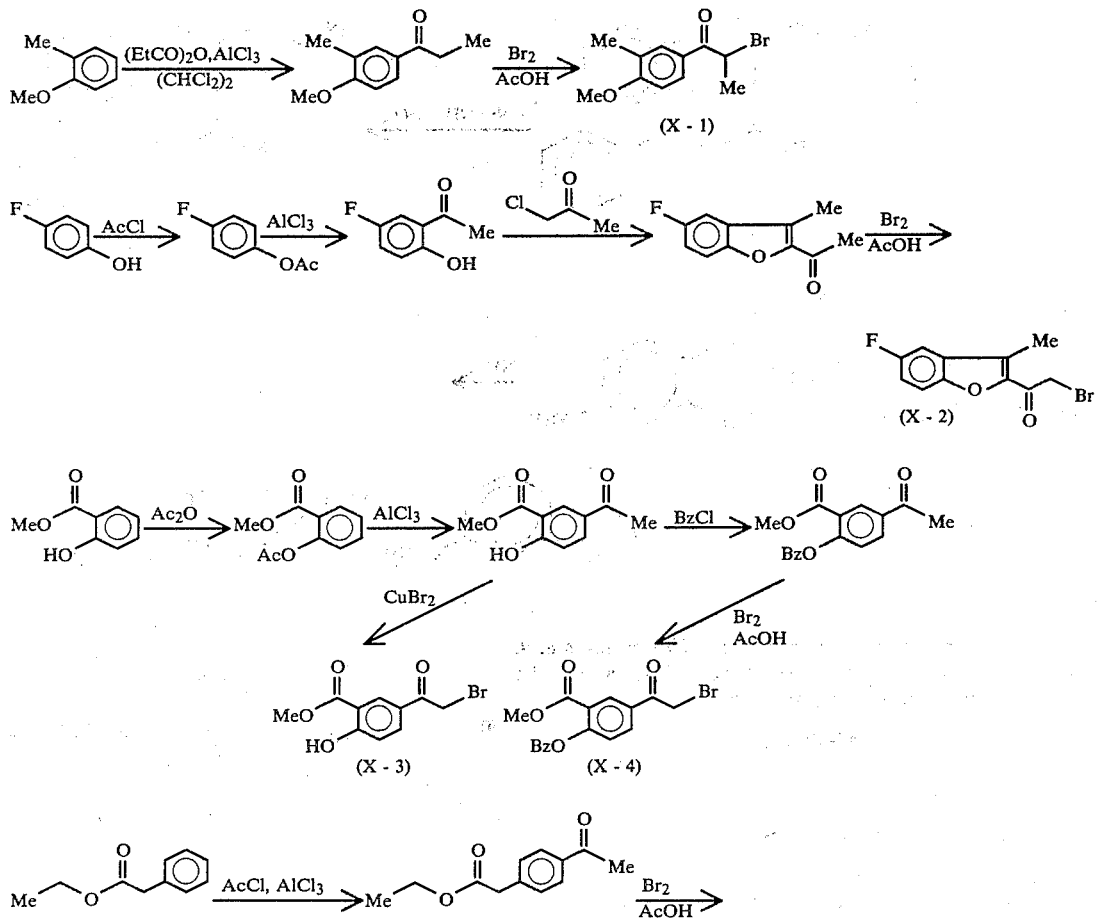 | (Reference Example 4) |
| X-2 | | (Reference Example 5) |
| X-3 | | Japanese published Examined Patent Application No. 43341/68 |
| X-4 | | J. Med. Chem. Vol. 20, 1029 (1977) |
| X-5 | | Ger. Offen. 2,430,077 (1975) |
| X-6 | | — |

The processes for the production of these compounds are shown by the following flow diagram, wherein Me represents a methyl group, Et represents an ethyl group, Bz represents a benzyl group and AC represents an acetyl group.

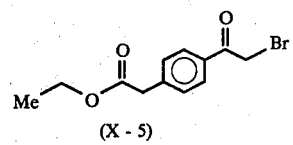

(X - 5)

Method 3

In order to obtain an amino-alcohol derivative having a terminal amide bond, a compound is used as the starting material whose moiety corresponding to the amide bond of the desired compound is an ester bond and whose residual moiety agrees with that of the desired compound. This starting compound is reacted with ammonia to convert the ester into an amide.

For example, the ester-bond-containing starting compound is dissolved in ethanol and the solution is poured into a pressure tube. Then, liquid ammonia is added thereto and the tube is sealed. The sealed tube is typically allowed to stand for 1-2 weeks at room temperature to convert the ester bond to an amide bond. Compounds 14, 15, 19, 21, 26, and 32 can be readily converted to Compound 11, 16, 20, 22, 30 and 34 respectively by this method.

Method 4

An amino-alcohol derivative having a terminal carboxy group is obtained by hydrolyzing a corresponding ester compound.

In this method, the corresponding ester-bond-containing compound is dissolved in ethanol. An acid, e.g. hydrochloric acid is added thereto, and the solution is heated under reflux. The hydrochloride of the desired compound is obtained by removing the solvent used from the resulting reaction solution and, if necessary, recrystallizing the hydrochloride from an organic solvent. Compound 17 can be obtained from the corresponding Compound 14 by this method.

Method 5

An amino-alcohol derivative having a terminal hydrazino group is obtained in the following manner. A corresponding ester compound is dissolved in ethanol, hydrazine hydrate is added thereto and the solution is heated under reflux. The desired compound is obtained by removing the solvent from the resulting reaction solution and, if necessary, recrystallizing the compound from an organic solvent. Compound 18 can be obtained from the corresponding Compound 14 by this method.

In addition to the above methods, compounds of the present invention can also be produced using known methods such as the following:

Method 6

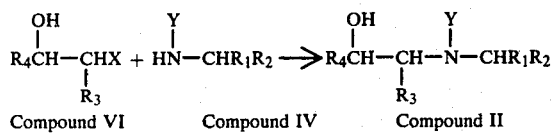

Compound VI    Compound IV    Compound II

The reaction is carried out under reflux in a solvent.

Method 7

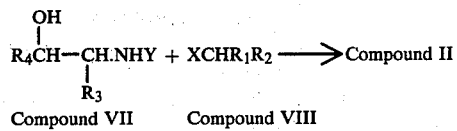

Compound VII    Compound VIII

The reaction is carried out under reflux in a solvent.

Method 8

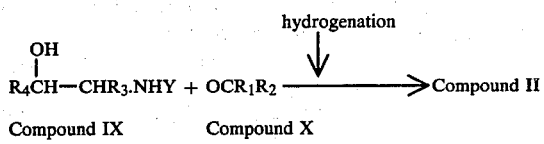

Compound IX    Compound X

Method 9

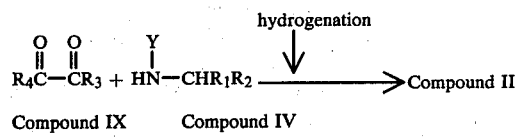

Compound IX    Compound IV

The reaction rapidly proceeds and Compound II is obtained by hydrogenating the imino compound formed with pd-c, $H_2$ or sodium borohydride.

Method 10

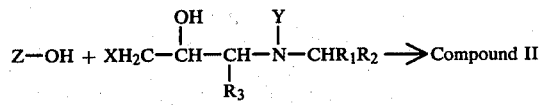

In the above formulae, Z represents a substituted phenyl group or a substituted heterocyclyl group, $R_1$, $R_2$, $R_3$, $R_4$ and Y have the same meaning as defined before and X represents a halogen atom.

The reactions in Methods 6 through 10 can be carried out by applying the methods disclosed in A. F. Crowther, et al.; Journal of Medicinal Chemistry 12, 638 (1969), H. H. Willrath, et al.; German Pat. No. 2,106,209, C. Kaiser, et al.; Journal of Medicinal Chemistry 18, 674 (1975), Japanese Published Examined Patent Applications No. 21775/66, No. 14541/67, No. 1984/67, No. 14942/67 and others.

All of the amino-alcohol derivatives obtained by these methods are weakly basic compounds. The acid addition salts thereof, e.g. inorganic acid addition salts such as hydrochloride, sulfate, hydrobromide, phosphate and the like and organic acid addition salts such as acetate, maleate, fumarate, tartrate, citrate, oxalate, benzoate and the like can be readily produced in a conventional manner.

Particularly preferred compounds of the present invention are identified below. The compound numbers are used in the Examples which follow to identify the particular compound.

(1) 1-(3-methylphenoxy)-3-(1,4-benzodioxane-2-methaneamino)-2-propanol
(2) 1-(4-acetamidophenoxy)-3-(1,4-benzodioxane-2-methaneamino)-2-propanol
(3) 1-(2-cyanophenoxy)-3-(1,4-benzodioxane-2-methaneamino)-2-propanol
(4) 1-(4-butyrylamido-2-acetyl)phenoxy-3-(1,4-benzodioxane-2-methaneamino)-2-propanol
(5) 1-(4-ethoxycarbonylmethyl)phenoxy-3-(1,4-benzodioxane-2-methaneamino)-2-propanol
(6) 1-(2,3-dimethylphenoxy)-3-(1,4-benzodioxane-2-methaneamino)-2-propanol
(7) 1-(1-naphthyloxy)-3-(1,4-benzodioxane-2-methaneamino)-2-propanol
(8) 1-(3-methyl-4-methoxy) phenyl-2-(1,4-benzodioxane-2-methaneamino)propanol
(9) 1-(5-fluoro-3-methyl-2-benzofuranyl)-2-(1,4-benzodioxane-2-methaneamino)ethanol
(10) 1-(3-methoxycarbonyl-4-hydroxy)phenyl-2-(1,4-benzodioxane-2-methaneamino)ethanol
(11) 1-(4-carbamoylmethylphenoxy)-3-(1-methyl-3-phenylpropylamino)-2-propanol
(12) 1-(2-cyanophenoxy)-3-(1-methyl-3-phenylpropylamino)-2-propanol
(13) 1-(2,3-dimethylphenoxy)-3-(1-methyl-3-phenylpropylamino)-2-propanol
(14) 1-(4-ethoxycarbonylmethylphenoxy)-3-(1-methyl-3-phenylpropylamino)-2-propanol
(15) 1-(2-methoxycarbonylphenoxy)-3-(1-methyl-3-phenylpropylamino)-2-propanol
(16) 1-(2-carbamoylphenoxy)-3-(1-methyl-3-phenylpropylamino)-2-propanol
(17) 1-(4-carboxymethylphenoxy)-3-(1-methyl-3-phenylpropylamino)-2-propanol
(18) 1-(4-hydrazinocarbonylmethylphenoxy)-3-(1-methyl-3-phenylpropylamino)-2-propanol
(19) 1-(3-ethoxycarbonylmethylphenoxy)-3-(1-methyl-3-phenylpropylamino)-2-propanol
(20) 1-(3-carbamoylmethylphenoxy)-3-(1-methyl-3-phenylpropylamino)-2-propanol
(21) 1-(4-ethoxycarbonylmethylphenyl)-2-(1-methyl-3-phenylpropylamino)ethanol
(22) 1-(4-carbamoylmethylphenyl)-2-(1-methyl-3-phenylpropylamino)ethanol
(23) 1-(4-acetamidophenoxy)-3-(1,4-benzodioxane-6-methaneamino)-2-propanol
(24) 1-{3,4-dihydro-1(2H)-naphthalenon-5-yl}oxy-3-(1,4-benzodioxane-6-methaneamino)-2-propanol
(25) 1-(4-carbamoylmethylphenoxy)-3-(1,4-benzodioxane-6-methaneamino)-2-propanol
(26) 1-(4-ethoxycarbonylmethylphenoxy)-3-{β-[N-benzyl-N-(1-methyl-2-phenoxyethyl)]aminoethyl}-amino-2-propanol
(27) 1-(4-acetamidophenoxy)-3-{β-[N-benzyl-N-(1-methyl-2-phenoxyethyl)]aminoethyl}amino-2-propanol
(28) 1-(4-butyrylamido-2-acetylphenoxy)-3-{β-[N-benzyl-N-(1-methyl-2-phenoxyethyl)]aminoethyl}-amino-2-propanol
(29) 1-(3-methylphenoxy)-3-{β-[N-benzyl-N-(1-methyl-2-phenoxyethyl)]aminoethyl}amino-2-propanol
(30) 1-(4-carbamoylmethylphenoxy)-3-{β-[N-benzyl-N-(1-methyl-2-phenoxyethyl)]aminoethyl}amino-2-propanol
(31) 1-(2-cyanophenoxy)-3-{1-methyl-2-(4-methoxyphenoxy)ethylamino}-2-proponol
(32) 1-(4-ethoxycarbonylmethylphenoxy)-3-{1-methyl-2-(4-methoxyphenoxy)ethylamino}-2-propanol
(33) 1-(4-acetamidophenoxy)-3-{1-methyl-2-(4-methoxyphenoxy)ethylamino}-2-propanol
(34) 1-(4-carbamoylmethylphenoxy)-3-{1-methyl-2-(4-methoxyphenoxy)ethylamino}-2-propanol The structural formulae of the compounds set forth above are shown in Table 4, where Me represents a methyl group, Et represents an ethyl group and Bz represents a benzyl group. In addition, the following abbreviations are used to represent $R_1$:

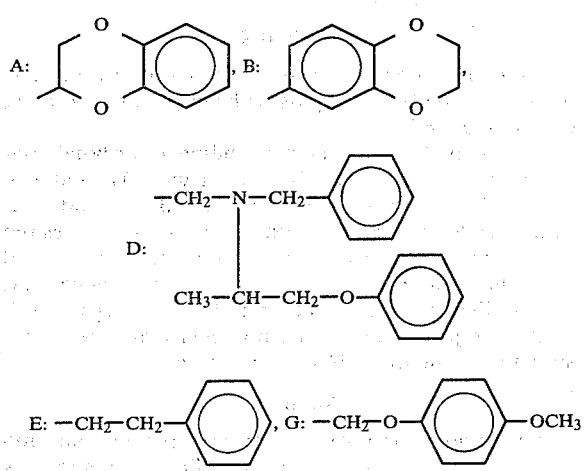

TABLE 4

| Compound number | Structural formula | $R_1$ | $R_2$ | $R_3$ | $R_4$ |
|---|---|---|---|---|---|
| 1 |  | A | H | H |  |
| 2 |  | A | H | H |  |

TABLE 4-continued

| Compound number | Structural formula | R₁ | R₂ | R₃ | R₄ |
|---|---|---|---|---|---|
| 3 | | A | H | H | |
| 4 | | A | H | H | |
| 5 | | A | H | H | |
| 6 | | A | H | H | |
| 7 | | A | H | H | |
| 8 | | A | H | Me | |
| 9 | | A | H | H | |
| 10 | | A | H | H | |
| 11 | | E | Me | H | |
| 12 | | E | Me | H | |
| 13 | | E | Me | H | |

TABLE 4-continued

| Compound number | Structural formula | R₁ | R₂ | R₃ | R₄ |
|---|---|---|---|---|---|
| 14 | EtO-C(=O)-CH₂-C₆H₄-O-CH₂-CH(OH)-CH₂-NH-CH(Me)-CH₂-C₆H₅ | E | Me | H | EtO-C(=O)-CH₂-C₆H₄-O- |
| 15 | 2-(MeO₂C)-C₆H₄-O-CH₂-CH(OH)-CH₂-NH-CH(Me)-CH₂-C₆H₅ | E | Me | H | 2-(MeO₂C)-C₆H₄-O- |
| 16 | 2-(H₂NCO)-C₆H₄-O-CH₂-CH(OH)-CH₂-NH-CH(Me)-CH₂-C₆H₅ | E | Me | H | 2-(H₂NCO)-C₆H₄-O- |
| 17 | HO-C(=O)-CH₂-C₆H₄-O-CH₂-CH(OH)-CH₂-NH-CH(Me)-CH₂-C₆H₅ | E | Me | H | HO-C(=O)-CH₂-C₆H₄-O- |
| 18 | H₂N-NH-C(=O)-CH₂-C₆H₄-O-CH₂-CH(OH)-CH₂-NH-CH(Me)-CH₂-C₆H₅ | E | Me | H | H₂N-NH-C(=O)-CH₂-C₆H₄-O- |
| 19 | MeO-C(=O)-CH₂-C₆H₄(3-O)-CH₂-CH(OH)-CH₂-NH-CH(Me)-CH₂-C₆H₅ | E | Me | H | MeO-C(=O)-CH₂-C₆H₄(3-O)- |
| 20 | H₂N-C(=O)-CH₂-C₆H₄(3-O)-CH₂-CH(OH)-CH₂-NH-CH(Me)-CH₂-C₆H₅ | E | Me | H | H₂N-C(=O)-CH₂-C₆H₄(3-O)- |
| 21 | MeO-C(=O)-CH₂-C₆H₄-CH(OH)-CH₂-NH-CH(Me)-CH₂-C₆H₅ | E | Me | H | MeO-C(=O)-CH₂-C₆H₅ |
| 22 | H₂N-C(=O)-CH₂-C₆H₄-CH(OH)-CH₂-NH-CH(Me)-CH₂-C₆H₅ | E | Me | H | H₂N-C(=O)-C₆H₄-Me |
| 23 | Me-C(=O)-NH-C₆H₄-O-CH₂-CH(OH)-CH₂-NH-CH₂-(2,3-dihydrobenzodioxinyl) | B | H | H | Me-C(=O)-NH-C₆H₄-O- |
| 24 | (4-oxo-naphth-1-yl)-O-CH₂-CH(OH)-CH₂-NH-CH₂-(2,3-dihydrobenzodioxinyl) | B | H | H | (ethoxy-naphth-oxo)- |
| 25 | H₂N-C(=O)-CH₂-C₆H₄-O-CH₂-CH(OH)-CH₂-NH-CH₂-(2,3-dihydrobenzodioxinyl) | B | H | H | H₂N-C(=O)-CH₂-C₆H₄-O- |

TABLE 4-continued

| Compound number | Structural formula | $R_1$ | $R_2$ | $R_3$ | $R_4$ |
|---|---|---|---|---|---|
| 26 | | D | H | H | |
| 27 | | D | H | H | |
| 28 | | D | H | H | |
| 29 | | D | H | H | |
| 30 | | D | H | H | |
| 31 | | G | Me | H | |
| 32 | | G | Me | H | |
| 33 | | G | Me | H | |
| 34 | | G | Me | H | |

The pharmacological activity of the compounds of the present invention is illustrated by the following experiments: (a) diastolic blood pressure (DBP) and systolic blood pressure (SBP), (b) organ blood flow, (c) $\alpha$, $\beta_1$, $\beta_2$ blocking activity, (d) heart rate, (e) changes in blood pressure of spontaneous hypertensive rats (SHR-BP) and (f) acute toxicity ($LD_{50}$).

In experiments (a), (b), (c) and (d), 3-4 male or female mongrel dogs (weight: 10-20 Kg) as one group were anesthetized by intravenous administration of 30 mg/kg of pentobarbital-Na. All compounds were dissolved in polyethylene glycol 400 and administered to the femoral vein.

Each test is described in detail below.

(a) Effect on diastolic blood pressure (DBP) and systolic blood pressure (SBP)

In this test, 1 mg/kg of each compound shown in Tables 5 and 7 is administered to the dogs and changes in blood pressure (mm Hg) are measured. A negative sign signifies a drop in blood pressure.

(b) Effect on organ blood flow M (%)

In this test, 1 mg/kg of each compound shown in Tables 5 and 7 is administered to the dogs and an electromagnetic probe is attached to the main artery of the dogs' organ to measure the flow of blood. The percentage change in organ blood flow as against the flow before administration of the test compounds is shown in Tables 5 and 7.

(c) α, β₁, β₂ blocking activity (c-1) α blocking activity

In this test, 3 μg/kg of Norepinephrine is intravenously administered to the dogs to cause an increase in systolic blood pressure. Percentage inhibition (%) of the increase by administration of 0.1 mg/kg of the test comounds is shown in Table 6.

(c-2) β₁ blocking activity

In this test, 0.5 μg/kg of Isoproterenol is intravenously administered to the dogs to cause an increase in the heart rate. Percentage inhibition (%) of the increase by administration of 0.1 mg/kg of the test compounds is shown in Table 6.

(c-3) β₂ blocking activity

In this test, 0.5 μg/kg of Isoproterenol is intravenously administered to the dogs to cause a decrease in diastolic blood pressure. Percentage inhibition (%) of the decrease by administration of 0.1 mg/kg of the test compounds is shown in Table 6. Labetalol {5-[1-hydroxy-2-(1-methyl-3-phenylpropyl) aminoethyl] salicylamide hydrochloride} having α- or β-adrenergic receptor blocking activity was used as a control.

(d) Effect on heart rate (beats/min.)

The decrease in heart rate by administration of 1 mg/kg of the test compounds to the dogs is shown in Table 7.

(e) Change in blood pressure (mm Hg) of spontaneous hypertensive rats (SHR)

In this test, 30 mg/kg of the test compounds is orally administered to SHR and changes in the blood pressure are measured by plethysmographic tail method. The change in blood pressure from the blood pressure before administration is shown in Table 5. A negative sign signifies a drop in blood pressure.

(f) LD₅₀ (g/kg)

The test compounds were orally administered to male dd-strain mice weighing 20–25 g.

TABLE 5

| Compound number | DBP/SBP mmHg | Organ blood flow Malleus | Organ blood flow Femoral Crotch | SHR-BP mmHg | LD₅₀ g/kg |
|---|---|---|---|---|---|
| 1 | −40/— | +67 | +35 | −28 | 1-2 |
| 2 | −50/— | +50 | +20 | −85 | 0.5-1 |
| 3 | −65/−34 | +18 | −21 | 0 | 0.42 |
| 4 | −55/−49 | −46 (0.1 mg administration) | −18 (0.1 mg administration) | −73 | >1 |
| 5 | −50/−40 | −84 | −26 | −60 | >1 |
| 6 | −28/−32 | −9 | +17 | 0 | >1 |
| 7 | −15/−18 | +59 | −36 | 0 | >1 |
| 8 | −17/−18 | −4 | −67 | 0 | 0.45 |
| 9 | −24/−25 | +35 | +42 | −48 | >1 |
| 10 | −5/−6 | −16 | −50 | −52 | |
| 23 | −30/−32 | +67 | +90 | 0 | >1 |
| 24 | −45/−15 | +60 | +106 | 0 | >1 |

TABLE 5-continued

| Compound number | DBP/SBP mmHg | Organ blood flow Malleus | Organ blood flow Femoral Crotch | SHR-BP mmHg | LD₅₀ g/kg |
|---|---|---|---|---|---|
| 25 | −33/−15 | +22 | +90 | 0 | >1 |

TABLE 6

| Compound number | α % | β₁ % | β₂ % | LD₅₀ g/Kg |
|---|---|---|---|---|
| 11* | −78 | −86 | −22 | >1 |
| 12* | −52 | −100 | −100 | 0.125-0.25 |
| 13 | −20 | −73 | −34 | 0.5-1.0 |
| 14 | +13 | −11 | +2 | >1 |
| 15 | −2 | −30 | −40 | 0.5-1.0 |
| 16 | −28 | −57 | −19 | 0.25-0.5 |
| 17 | +15 | +13 | −13 | >1 |
| 18 | +10 | −3 | +2 | >1 |
| 19 | +23 | −7 | +14 | >1 |
| 20 | +7 | −9 | +9 | >1 |
| 21 | +9 | −10 | −8 | >1 |
| 22 | +19 | −8 | −11 | >1 |
| 31 | −20 | −54 | −30 | 0.125-0.25 |
| 32 | 0 | −11 | −2 | >1 |
| 33 | −21 | −52 | −13 | >1 |
| 34 | −36 | −55 | −57 | >1 |
| Reference compound | −32 | −69 | −50 | 0.76-1 |

*: Dose of compound: 1 mg/kg

TABLE 7

| Compound number | DBP/SBP mmHg | Heart rate beats/min. | Organ blood flow Malleus % | Organ blood flow Crotch % | LD₅₀ g/kg |
|---|---|---|---|---|---|
| 26 | −16/−22 | −20 | +67 | −12 | >1 |
| 27 | −24/−27 | −13 | +100 | +3 | >1 |
| 28 | −17/−18 | −8 | +61 | +4 | 1-2 |
| 29 | −18/−14 | −4 | +100 | −45 | — |
| 30 | −4/−7 | −5 | +10 | −19 | — |

As is apparent from Tables 5–7, the compounds of the present invention have a significant α and β adrenergic receptor blocking effect and also effectively increase organ blood flow. As such, the compounds are useful as medicaments for cardiovascular diseases such as hypertension, angina pectoris and cerebrovascular diseases.

In view of the pharmacological activity exhibited, the compounds of the present invention may be used in various pharmaceutical forms for administration. Pharmaceutical compositions of the present invention are prepared by uniformly mixing an effective amount of the compound as the active ingredient, in free form or as an acid addition salt, with a pharmaceutically acceptable carrier. The carrier may take various forms depending on the pharmaceutical form suitable for administration. It is preferable that the pharmaceutical composition be in single administration form suitable for administration per os or by injection.

In preparation of the compositions for oral administration, any useful pharmaceutical carrier may be used. For example, oral liquid preparations such as suspensions and syrups can be prepared using water, glycols, oils, alcohols and the like. Powders, pills, capsules and tablets can be prepared using disintegrators and the like.

Tablets and capsules are the most useful single oral administration forms because of the ease of administration. To make tablets and capsules solid pharmaceutical carriers are used.

Where pharmaceutical compositions for parenteral administration is desired, the carrier for the most part consists of sterile aqueous solutions. The carrier, however, may also contain other components to help the dissolution of the amino-alcohol derivative.

For example, an injection solution can be prepared using a carrier consisting of a mixture of salt solution and glucose solution or saline solution and glucose solution. The suspensions for injection can be prepared using an appropriate liquid carrier, disperding agent and the like. Though the amount of the active ingredient can be varied in a rather wide range, 1-50 mg/kg/day in one dose or several divided doses is generally considered to be effective.

Certain specific embodiments of the invention are illustrated by the following representative examples.

EXAMPLE 1

Preparation of Compound 4

In this example, 2.8 g of 1-(4-butyrylamido-2-acetyl) phenoxy-2,3-epoxypropane and 1.7 g of 1,4-benzodioxane-2-methaneamine are refluxed in 70 ml of 99.5% ethanol for 1 hour. After completion of the reaction, ethanol is distilled away from the solution under reduced pressure. The residue is recrystallized twice from 50 ml of toluene to obtain 1.3 g of 1-(4-butyrylamido-2-acetyl) phenoxy-3-(1,4-benzodioxane-2-methaneamino)-2-propanol.

(Yield: 29%).

Melting point: 133°-135° C.

Infra-red absorption spectrum (KBr tablet, cm$^{-1}$): 3340, 2930, 1650, 1550, 1495, 1265.

N.M.R. spectrum (CDCl$_3$, δ, p.p.m): 1.12(t, 3H), 2.57(s, 3H), 1.40-4.43(m, 16H), 6.63-8.00(m, 8H).

Elementary analysis as $C_{24}H_{30}N_2O_6$(%):

|  | C | H | N |
|---|---|---|---|
| Calculated: | 65.14 | 6.83 | 6.33 |
| Found: | 65.07 | 7.10 | 6.45 |

Examples 2-13

The following compounds are obtained by repeating the same procedure as in Example 1 but varying the reaction conditions as shown in Table 8.

TABLE 8

| Example | Compound number | Epoxy compound/g | Amine/g | Yield (g) | Yield (%) | Note |
|---|---|---|---|---|---|---|
| 2 | 1 | EP-1/1.6 | AM-1/1.7 | 1.0 | 30 | *1 |
| 3 | 2 | EP-2/2.1 | AM-1/1.7 | 0.6 | 16 | *1 |
| 4 | 3 | EP-3/1.8 | AM-1/1.7 | 1.7 | 50 | *1 |
| 5 | 5 | EP-5/2.4 | AM-1/1.7 | 0.8 | 20 | *1 |
| 6 | 6 | EP-6/1.8 | AM-1/1.7 | 0.8 | 23 |  |
| 7 | 7 | EP-7/2.0 | AM-1/1.7 | 1.7 | 42 | *1, *2 |
| 8 | 13 | EP-6/1.8 | AM-3/1.5 | 1.7 | 52 |  |
| 9 | 23 | EP-2/2.1 | AM-8/2.0 | 1.8 | 49 |  |
| 10 | 24 | EP-13/2.2 | AM-8/2.0 | 1.8 | 47 |  |
| 11 | 25 | EP-8/4.0 | AM-8/3.3 | 0.4 | 6 | *1 |
| 12 | 26 | EP-5/4.7 | AM-7/5.7 | 2.3 | 19 | *1, *2 |
| 13 | 29 | EP-1/1.6 | AM-7/2.9 | 1.6 | 36 | *1 |

*1: The desired compound is purified by silicagel column chromatography instead of recrystallization from toluene shown in Example 1.
*2: The free base obtained is dissolved in a solvent and hydrogen chloride gas is bubbled thereinto to obtain the desired compound as the hydrochloride salt in crystalline form.

Compound 1

1-(3-methylphenoxy)-3-(1,4-benzodioxane-2-methaneamino)-2-propanol.

Melting point: 90°-92° C.

Infra-red absorption spectrum (KBr tablet, cm$^{-1}$): 2920, 1595, 1495, 1290, 1265, 1175.

N.M.R. spectrum (CDCl$_3$; δ, p.p.m): 2.30(s, 3H), 2.47-4.53(m, 12H), 6.53-7.40(m, 8H).

Elementary analysis as $C_{19}H_{23}NO_4$ (%):

|  | C | H | N |
|---|---|---|---|
| Calculated: | 69.28 | 7.04 | 4.25 |
| Found: | 69.03 | 6.98 | 4.52 |

Compound 2

1-(4-acetamidophenoxy)-3-(1,4-benzodioxane-2-methaneamino)-2-propanol.

Melting point: 114°-116° C.

Infra-red absorption spectrum (KBr tablet, cm$^{-1}$): 2930, 1665, 1515, 1495, 1265, 1245.

N.M.R. spectrum (CDCl$_3$+d$_6$ -DMSO, δ, p.p.m): 2.70(s, 3H), 2.33-4.47(m, 12H), 6.67-7.73(m, 8H), 9.30(s, 1H).

Elementary analysis as $C_{20}H_{24}N_2O_5$ (%):

|  | C | H | N |
|---|---|---|---|
| Calculated: | 64.50 | 6.50 | 7.52 |
| Found: | 64.77 | 6.55 | 7.38 |

Compound 3

1-(2-cyanophenoxy)-3-(1,4-benzodioxane-2-methaneamino)-2-propanol.

Melting point: 83°-85° C.

Infra-red absorption spectrum (KBr tablet, cm$^{-1}$): 2920, 2230, 1600, 1495, 1295, 1265.

N.M.R. spectrum (CDCl$_3$, δ, p.p.m.): 2.67-3.20(m, 6H), 3.80-4.40(m, 6H), 6.70(s, 4H), 6.70-7.60(m, 4H).

Elementary analysis as $C_{19}H_{20}N_2O_4$ (%):

|  | C | H | N |
|---|---|---|---|
| Calculated: | 67.05 | 5.92 | 8.23 |
| Found: | 66.84 | 6.04 | 8.20 |

Compound 5

1-(4-ethoxycarbonylmethyl) phenoxy-3-(1,4benzodioxane-2-methaneamino)-2-propanol.

Melting point: 82°-85° C.

Infra-red absorption spectrum (KBr tablet, cm$^{-1}$): 2900, 1725, 1495, 1300, 1255, 1035.

N.M.R. spectrum (CDCl$_3$, δ, p.p.m.): 1.22(t, 3H), 2.42-4.50(m, 16H), 6.70-7.27(m, 8H)

Elementary analysis as $C_{22}H_{27}NO_6$ (%):

|  | C | H | N |
|---|---|---|---|
| Calculated: | 65.82 | 6.78 | 3.49 |
| Found: | 66.01 | 6.71 | 3.27 |

Compound 6

1-(2,3-dimethylphenoxy)-3-(1,4-benzodioxane-2-methaneamino)-2-propanol.

Melting point: As the desired compound was obtained as a concentrated dry powder, a clear melting point thereof was not shown.

Infra-red absorption spectrum (KBr tablet, cm$^{-1}$): 2920, 1595, 1500, 1470, 1265, 1110.

N.M.R. spectrum (CDCl$_3$+d$_6$-DMSO, δ, p.p.m.): 2.13(s, 3H), 2.22(s, 3H), 2.37-4.50(m, 12H), 6.43-7.40(m, 7H).

Elementary analysis as C$_{20}$H$_{25}$NO$_4$ (%):

|  | C | H | N |
|---|---|---|---|
| Calculated: | 69.95 | 7.34 | 4.08 |
| Found: | 70.22 | 7.08 | 4.11 |

Compound 7

1-(1-naphthyloxy)-3-(1,4-benzodioxane-2-methaneamino)-2-propanol hydrochloride.

Melting point: 166°-168° C.

Infra-red absorption spectrum (KBr tablet, cm$^{-1}$): 2920, 1595, 1500, 1400, 1270, 1105.

N.M.R. spectrum (measured as free base, CDCl$_3$, δ, p.p.m.): 2.70(s, 2H), 2.83-4.50(m, 10H), 6.82(s, 4H), 7.10-8.40(m, 7H).

Elementary analysis as C$_{22}$H$_{24}$NO$_4$Cl (%):

|  | C | H | N |
|---|---|---|---|
| Calculated: | 65.75 | 6.02 | 3.49 |
| Found: | 65.98 | 5.93 | 3.26 |

Compound 13

1-(2,3-dimethylphenoxy)-3-(1-methyl-3-phenylpropylamino)-2-propanol.

Melting point: 82°-84° C.

Infra-red absorption spectrum (KBr tablet, cm$^{-1}$): 2920, 1590, 1470, 1260, 1110, 1090.

N.M.R. spectrum (CDCl$_3$, δ, p.p.m.): 1.13(d, 3H), 2.17(s, 3H), 2.27(s, 3H), 1.40-4.23(m, 12H), 6.48-7.47(m, 8H).

Elementary analysis as C$_{21}$H$_{29}$NO$_2$ (%):

|  | C | H | N |
|---|---|---|---|
| Calculated: | 77.02 | 8.93 | 4.28 |
| Found: | 76.98 | 9.01 | 4.03 |

Compound 23

1-(4-acetamidophenoxy)-3-(1,4-benzodioxane-6-methaneamino)-2-propanol.

Melting point: 149°-151° C.

Infra-red absorption spectrum (KBr tablet, cm$^{-1}$): 3270, 1660, 1515, 1290, 1250, 1035.

N.M.R. spectrum (d$_6$-DMSO, δ, p.p.m.): 1.99(s, 3H), 4.17(s, 4H), 2.95-4.00(m, 9H), 6.70(s, 3H), 6.80(d, 2H), 7.43(d, 2H), 9.67(s, 1H).

Elementary analysis as C$_{20}$H$_{24}$N$_2$O$_5$ (%):

|  | C | H | N |
|---|---|---|---|
| Calculated: | 64.50 | 6.50 | 7.52 |
| Found: | 64.71 | 6.53 | 7.29 |

Compound 24

1-{3,4-dihydro-1(2H)-naphtalenon-5yl} oxy-3-(1,4-benzodioxane-6-methaneamino)-2-propanol.

Melting point: 125°-130° C.

Infra-red absorption spectrum (KBr tablet, cm$^{-1}$): 3270, 2930, 1690, 1585, 1460, 1285.

N.M.R. spectrum (d$_6$-DMSO, 67, p.p.m.): 1.90-4.03(m, 15H), 4.13(s, 4H), 6.57-7.43(m, 6H).

Elementary analysis as C$_{22}$H$_{25}$NO$_5$ (%):

|  | C | H | N |
|---|---|---|---|
| Calculated: | 68.91 | 6.57 | 3.65 |
| Found: | 68.87 | 6.50 | 3.48 |

Compound 25

1-(4-carbamoylmethylphenoxy)-3-(1,4-benzodioxane-6-methaneamino)-2-propanol.

Melting point: 133°-136° C.

Infra-red absorption spectrum (KBr tablet, cm$^{-1}$): 3350, 3170, 1640, 1510, 1290, 1240.

N.M.R. spectrum (d$_6$-DMSO, δ, p.p.m.): 3.26(s, 2H), 3.83(s, 2H), 4.15(s, 4H), 2.77-4.17(m, 7H), 6.43-7.40(m, 9H).

Elementary analysis as C$_{20}$H$_{24}$N$_2$O$_5$ (%):

|  | C | H | N |
|---|---|---|---|
| Calculated: | 64.50 | 6.50 | 7.52 |
| Found: | 64.22 | 6.57 | 7.28 |

Compound 26

1-(4-ethoxycarbonylmethylphenoxy)-3-{β-[N-benzyl-N-(1-methyl-2-phenoxyethyl)] aminoethyl= amino-2-propanol dihydrochloride.

Melting point: As the desired compound was obtained as a concentrated dry powder, a clear melting point thereof was not shown.

Infra-red absorption spectrum (KBr tablet, cm$^{-1}$): 2930, 1730, 1615, 1515, 1240, 1030.

N.M.R. spectrum (measured as free base, CDCl$_3$, δ, p.p.m.): 1.15(d, 3H), 1.23(t, 3H), 2.33-4.37(m, 19H), 6.67-7.50(m, 14H).

Elementary analysis as C$_{31}$H$_{42}$N$_2$O$_5$Cl$_2$ (%):

|  | C | H | N |
|---|---|---|---|
| Calculated: | 62.73 | 7.13 | 4.72 |
| Found: | 62.58 | 6.99 | 4.70 |

Compound 29

1-(3-methylphenoxyl)-3-{β-[N-benzyl-N-(1-methyl-2-phenoxyethyl)] aminoethyl} amino-2-propanol (This compound is obtained as a free base in the form of an oil).

Infra-red absorption spectrum (NaCl cell, cm$^{-1}$): 2920, 1600, 1495, 1245, 1160, 1040.

N.M.R. spectrum (CDCl₂, δ, p.p.m.): 1.12(d, 3H), 2.30(s, 3H), 2.40-4.23(m, 16H), 6.43-7.53(m, 14H).

Elementary analysis as $C_{28}H_{36}N_2O_3$ (%):

|  | C | H | N |
|---|---|---|---|
| Calculated: | 74.97 | 8.09 | 6.24 |
| Found: | 75.03 | 8.37 | 5.98 |

EXAMPLE 14

Preparation of Compound 12

In this example, 1.5 g of 1-methyl-3-phenylpropylamine and 1.8 g of 1-(2-cyanophenoxy)-2,3-epoxypropane are refluxed for 1.5 hours in 50 ml of 99.5% ethanol. After completion of the reaction, the reaction solution is concentrated under reduced pressure. The residue is then charged on a column packed with silica gel and the elution is carried out with methanol. The main fraction of the eluate is concentrated under reduced pressure.

Then, the residue is recrystallized from 200 ml of n-hexane to obtain 20 g of 1-(2-cyanophenoxy)-3-(1-methyl-3-phenylpropylamino)-2-propanol as crystals. (Yield: 62%)

Melting point: 63°-66° C.

Infra-red absorption spectrum (KBr tablet, cm⁻¹): 2920, 2230, 1600, 1495, 1455, 1290.

N.M.R. spectrum (CDCl₃, δ, p.p.m.): 1.13(d, 3H), 1.33-4.43(m, 12H), 6.80-7.73(m, 9H).

Elementary analysis as $C_{20}H_{24}N_2O_2$ (%):

|  | C | H | N |
|---|---|---|---|
| Calculated: | 74.05 | 7.46 | 8.63 |
| Found: | 73.79 | 7.19 | 8.59 |

EXAMPLE 15

Preparation of Compound 9

In this example, 5.1 g of N-benzyl-1,4-benzodioxane-2-methaneamine is dissolved in 50 ml of acetonitrile. To the solution is added 2.7 g of 2-bromoacetyl-3-methyl-5-fluorobenzofuran under ice-cooling and the mixture is stirred for 3 hours under ice-cooling. Then, 80 ml of 99.5% ethanol and 0.5 g of sodium borohydride are added thereto and the mixture is allowed to stand overnight at room temperature. The reaction solution is concentrated to dryness under reduced pressure. To the residue is added 100 ml of water and the solution is extracted twice with 100 ml of ether. The extract is dehydrated and then concentrated under reduced pressure. The resulting residue is then charged on a column packed with silica gel and the elution is carried out with chloroform to obtain 3.7 g of an oily 2-(N-benzyl-1-,4-benzodioxane-2-methaneamino)-1-(3-methyl-5-fluoro-2-benzofuranyl) ethanol as a main fraction. The compound obtained is dissolved in 200 ml of 99.5% ethanol and then 1 ml of concentrated hydrochloric acid and 0.5 g of 10% palladium carbon are added thereto for hydrogenolysis.

After completion of the reaction, palladium carbon is filtered off. The resulting filtrate is concentrated under reduced pressure and the residue is reslurried in ether to obtain 2.3 g of 1-(5-fluoro-3-methyl-2-benzofuranyl)-2(1,4-benzodioxane-2-methaneamino) ethanol hydrochloride as crystals. (Yield: 58%).

Melting point: 181°-183° C.

Infra-red absorption spectrum (KBr tablet, cm⁻¹): 2940, 1600, 1500, 1480, 1260, 1180.

N.M.R. spectrum (d₆-DMSO, δ, p.p.m.): 2.27(s, 3H), 2.43-5.67(m, 9H), 6.70-7.60(m, 7H), 9.86(s, 2H).

Elementary analysis as $C_{20}H_{21}NO_4ClF$ (%):

|  | C | H | N |
|---|---|---|---|
| Calculated: | 60.99 | 5.38 | 3.56 |
| Found: | 60.78 | 5.09 | 3.61 |

EXAMPLES 16-10

Compounds 10, 21 and 8 are obtained by using the compounds shown in Table 9 as starting materials and repeating the same procedures as in Example 15.

TABLE 9

| Example | Compound number | Compound V/g | Amine/g | Yield (g) | Yield (%) |
|---|---|---|---|---|---|
| 16 | 10 | X-4/7.2 | AM-2/10.2 | 6.0 | 76 |
| 17 | 21 | X-5/5.7 | AM-4/9.6 | 2.0 | 25 |
| 18* | 8 | X-1/2.6 | AM-1/1.7 | 0.8 | 23 |

*Ethanol is used as a solvent and hydrogenolysis is not carried out.

Compound 10

1-(3-methoxycarbonyl-4-hydroxy) phenyl-2-(1,4-benzodioxane-2-methaneamino) ethanol hydrochloride.

Melting point: 189°-192° C.

Infra-red absorption spectrum (KBr tablet, cm⁻¹): 2940, 1680, 1495, 1440, 1265, 1210.

N.M.R. spectrum (d₆-DMSO, δ, p.p.m.): 3.90(s, 3H), 2.33-5.00(m, 12H), 6.83(s, 4H), 6.80-8.80(m, 3H).

Elementary analysis as $C_{19}H_{22}NO_6Cl$ (%):

|  | C | H | N |
|---|---|---|---|
| Calculated: | 57.65 | 5.60 | 3.54 |
| Found: | 57.24 | 5.61 | 3.73 |

Compound 21

1-(4-ethoxycarbonylmethylphenyl)-2-(1-methyl-3-phenylpropylamino) ethanol hydrochloride.

Melting point: 96°-98° C.

Infra-red absorption spectrum (K3r tablet, cm⁻¹): 2980, 1735, 1425, 1220, 1150, 1030.

N.M.R. spectrum (measured as free base, CDCl₃, δ, p.p.m.): 0.92-1.30(m, 6H), 1.39-4.82(m, 9H), 3.49(s, 2H), 4.03(q, 2H), 7.07(s, 4H), 7.17(s, 5H).

Elementary analysis as $C_{22}H_{30}NO_3Cl$ (%):

|  | C | H | N |
|---|---|---|---|
| Calculated: | 67.42 | 7.72 | 3.57 |
| Found: | 67.54 | 7.81 | 3.44 |

Compound 8

1-(3-methyl-4-methoxy) phenyl-2-(1,4-benzodioxane-2-methaneamino) propanol.

Melting point: 181°-183° C.

Infra-red absorption spectrum (KBr tablet, cm⁻¹): 2920, 1595, 1495, 1255, 1130, 1035.

N.M.R. spectrum (CDCl₃, δ, p.p.m.): 0.92(d, 3H), 2.22(s, 3H), 3.79(s, 3H), 2.37–4.77(m, 9H), 6.67–7.33(m, 7H).

Elementary analysis as $C_{20}H_{25}NO_4$ (%):

|  | C | H | N |
|---|---|---|---|
| Calculated: | 69.95 | 7.34 | 4.08 |
| Found: | 69.72 | 7.39 | 4.16 |

EXAMPLE 19

Preparation of Compound 27

In this example, 2.8 g of N-benzyl-N-(1-methyl-2-phenoxyethyl) ethylenediamine and 2.1 g of 1-(4-acetamidophenoxy)-2,3-epoxypropane are refluxed for 1 hour in 40 ml of 99.5% ethanol. After completion of the reaction, the reaction solution is concentrated under reduced pressure. The resulting residue is then charged on a column packed with silica gel and the elution is carried out with methanol. The main fraction of the eluate is concentrated under reduced pressure to obtain 1-(4-acetamidophenoxy)-3-{β-[N-benzyl-N-(1-methyl-2-phenoxyethyl)] aminoethyl}amino-2-propanol as an oily free base. The compound obtained is dissolved in benzene-ether and hydrogen chloride gas is bubbled thereinto to obtain 0.9 g of the dihydrochloride as crystals.

(Yield: 16%).

Melting point: 70°–73° C.

Infra-red absorption spectrum (KBr tablet, cm⁻¹): 2920, 1665, 1600, 1510, 1240, 1035.

N.M.R. spectrum (measured as free base, CDCl₃, δ, p.p.m.): 1.16(d, 3H), 2.12(s, 3H), 2.30–4.53(m, 16H), 6.63–7.97(m, 15H).

Elementary analysis as $C_{29}H_{39}N_3O_4Cl_2$ (%):

|  | C | H | N |
|---|---|---|---|
| Calculated: | 61.70 | 6.96 | 7.44 |
| Found: | 61.65 | 6.68 | 7.50 |

EXAMPLE 20

Preparation of Compound 28

In this example, 2.8 g of N-benzyl-N-(1-methyl-2-phenoxyethyl)ethylenediamine and 2.8 g of 1-(2-acetyl-4-butyrylaminodiphenoxy)-2,3-epoxypropane are refluxed for 2 hours in 50 ml of 99.5% ethanol. After completion of the reaction, the reaction solution is concentrated under reduced pressure. The resulting residue is then charged on a column packed with silica gel and the elution is carried out with methanol. The main fraction of the eluate is concentrated under reduced pressure to obtain 1-(4-butyrylamido-2-acetylphenoxy)-3-{β-[N-benzyl-N-(1-methyl-2-phenoxyethyl)] aminoethyl} amino-2-propanol as an oily free base. The desired compound obtained is dissolved in benzene-ether and hydrogen chloride gas is bubbled thereinto to obtain 1.1 g of the dihydrochloride. (Yield: 17%).

Melting point: 62°–65° C.

Infra-red absorption spectrum (KBr tablet, cm⁻¹): 2950, 1660, 1600, 1495, 1235, 1025.

N.M.R. spectrum (measured as free base, CDCl₃, δ, p.p.m.): 1.13(d, 3H), 1.16(t, 3H), 2.58(s, 3H), 1.40–4.57(m, 20H) 6.65–8.30(m, 14H).

Elementary analysis as $C_{33}H_{45}N_3O_5Cl_2$ (%):

|  | C | H | N |
|---|---|---|---|
| Calculated: | 62.45 | 7.15 | 6.62 |
| Found: | 62.17 | 7.00 | 6.67 |

EXAMPLE 21

Preparation of Compound 14

In this example, 24.0 g of N-benzyl-1-methyl-3-phenylpropylamine and 23.6 g 1-(4-ethoxycarbonylmethylphenoxy)-2,3-epoxypropane are refluxed for 1 hour in 200 ml of 99.5% ethanol. Then, 10 ml of concentrated hydrochloric acid and 2.0 g of 10% palladium-carbon are added thereto and hydrogenolysis is carried out at room temperature and at atmospheric pressure. After completion of the reaction, palladium-carbon is filtered off from the solution. The resulting filtrate is concentrated under reduced pressure and the residue is dissolved in 1 l of water and washed twice with 200 ml of ether. After washing, the pH of the aqueous solution is adjusted to 11.5 and the solution is extracted three times with 200 ml of ether.

The extract is dehydrated and concentrated under reduced pressure to obtain 34.0 g of 1-(4-ethoxycarbonylmethylphenoxy)-3-(1-methyl-3-phenylpropylamino)-2-propanol as an oily free base. (Yield: 81%). Then, 4.0 g of the desired compound is dissolved in 100 ml of ether and hydrogen chloride gas is bubbled thereinto to obtain 4.0 g of the hydrochloride as crystals.

Melting point: 80°–83° C.

Infra-red absorption spectrum (KBr tablet, cm⁻¹): 2930, 1735, 1515, 1250, 1150, 1050.

N.M.R. spectrum (measured as free base, CDCl₃, δ, p.p.m.): 1.05(t, 3H), 1.12(d, 3H), 1.40–4.43(m, 16H), 6.37–7.60(m, 9H).

Elementary analysis as $C_{23}H_{32}NO_4Cl$ (%):

|  | C | H | N |
|---|---|---|---|
| Calculated: | 65.47 | 7.64 | 3.32 |
| Found: | 65.55 | 7.60 | 3.03 |

EXAMPLES 22–26

Compounds 15, 19, 31, 32 and 33 are obtained by repeating the same procedures as in Example 21 except using the starting compounds shown in Table 10. The properties of the compounds obtained are shown below.

In Examples 25 and 26, the desired compounds are obtained as the free bases thereof. In Example 23, the free base is dissolved in a solvent and fumaric acid is added thereto, whereby the desired compound is obtained as the fumarate salt.

TABLE 10

| Example | Compound number | Epoxy/g | Amine/g | Yield (g) | Yield (%) |
|---|---|---|---|---|---|
| 22 | 15 | EP-9/6.2 | AM-4/7.2 | 4.3 | 44 |
| 23 | 19 | EP-11/4.0 | AM-4/4.1 | 4.3 | 57 |
| 24 | 31 | EP-3/1.8 | AM-6/2.7 | 1.3 | 33 |
| 25 | 32 | EP-5/4.7 | AM-6/5.4 | 4.5 | 54 |
| 26 | 33 | EP-2/2.1 | AM-6/2.7 | 2.8 | 72 |

Compound 15

1-(2-methoxycarbonylphenoxy)-3-(1-methyl-3-phenylpropylamino)-2-propanol hydrochloride.
Melting point: 124°–127° C.
Infra-red absorption spectrum (KBr tablet, cm$^{-1}$): 3180, 2940, 2780, 1725, 1250, 1085.
N.M.R. spectrum (measured as free base CCl$_4$, δ, p.p.m.): 1.07(d, 3H), 3.73(s, 3H), 1,31–4.25(m, 12H), 6.67–7.93(m, 9H).
Elementary analysis as $C_{21}H_{28}NO_4Cl$ (%):

|  | C | H | N |
|---|---|---|---|
| Calculated: | 64.03 | 7.16 | 3.56 |
| Found: | 64.05 | 7.08 | 3.29 |

Compound 19

1-(3-ethoxycarbonylmethylphenoxy)-3-(1-methyl-3-phenylpropylamino)-2-propanol fumarate.
Melting point: 86°–89° C.
Infra-red absorption spectrum (KBr tablet, cm$^{-1}$): 2930, 1730, 1600, 1260, 1155, 1030.
N.M.R. spectrum (measured as free base, CDCl$_3$, δ, p.p.m.): 1.01–1.33(m, 6H), 3.48(s, 2H), 1.45–4.77(m, 14H), 6.57–7.40(m, 9H).
Elementary analysis as $C_{25}H_{33}NO_6$ (%):

|  | C | H | N |
|---|---|---|---|
| Calculated: | 67.70 | 7.50 | 3.16 |
| Found: | 67.42 | 7.52 | 2.97 |

Compound 31

1-(2-cyanophenoxy)-3-{1-methyl-2-(4-methoxyphenoxy)ethylamino}-2-propanol hydrochloride.
Melting point: 128°–132° C.
Infra-red absorption spectrum (KBr tablet, cm$^{-1}$): 2940, 2680, 2230, 1605, 1230, 1035.
N.M.R. spectrum (measured as free base, CCl$_4$, δ, p.p.m.): 1.09(d, 3H), 3.61(s, 3H), 2.50–4.33(m, 10H), 6.62(s, 4H), 6.63–7.63(m, 4H).
Elementary analysis as $C_{20}H_{25}N_2O_4Cl$ (%):

|  | C | H | N |
|---|---|---|---|
| Calculated: | 61.14 | 6.41 | 7.13 |
| Found: | 61.02 | 6.23 | 6.89 |

Compound 32

1-(4-ethoxycarbonylmethylphenoxy)-3-{1-methyl-2-(4-methoxyphenoxy) ethylamino}-2-propanol.
Melting point: 85°–87° C.
Infra-red absorption spectrum (KBr tablet, cm$^{-1}$): 2920, 1735, 1515, 1230, 1165, 1040.
N.M.R. spectrum (CDCl$_3$, δ, p.p.m.): 1.10–1.33(m, 6H), 3.71(s, 3H), 2.60–4.32(m, 14H), 6.57–7.27(m, 8H).
Elementary analysis as $C_{23}H_{31}NO_6$ (%):

|  | C | H | N |
|---|---|---|---|
| Calculated: | 66.17 | 7.48 | 3.35 |
| Found: | 66.41 | 7.52 | 3.07 |

Compound 33

1-(4-acetamidophenoxy)-3-{1-methyl-2-(4-methoxyphenoxy) ethylamino}-2-propanol.
Melting point: 123°–128° C.
Infra-red absorption spectrum (KBr tablet, cm$^{-1}$): 3260, 2920, 1655, 1515, 1230, 1040.
N.M.R. spectrum (d$_6$-DMSO, δ, p.p.m.): 1.08(d, 3H), 2.02(s, 3H), 3.68(s, 3H), 2.31–4.10(m, 10H), 6.57–7.63(m, 8H), 9.63(s, 1H).
Elementary analysis as $C_{21}H_{28}N_2O_5$ (%):

|  | C | H | N |
|---|---|---|---|
| Calculated: | 64.93 | 7.26 | 7.21 |
| Found: | 65.01 | 7.21 | 6.98 |

EXAMPLE 27

Preparation of Compound 11

In this example, 1.7 g of 1-(4-ethoxycarbonylmethylphenoxy)-3-(1-methyl-3-phenylpropylamino)-2-propanol (Compound 14) is dissolved in 100 ml of ethanol and the solution is poured into a pressure tube. Then, 100 ml of liquid ammonia is added thereto. The tube is sealed and is allowed to stand for 10 days at room temperature. After completion of the reaction, ethanol is distilled away from the solution under reduced pressure. The residue is recrystallized from methylisobutylketone to obtain 0.9 g of 1-(4-carbamoylmethylphenoxy)-3-(1-methyl-3-phenylpropylamino)-2-propanol. (Yield: 57%).
Melting point: 106°–109° C.
Infra-red absorption spectrum (KBr tablet, cm$^{-1}$): 3360, 2920, 1635, 1515, 1415, 1245.
N.M.R. spectrum (CDCl$_3$+d$_6$-DMSO, δ, p.p.m.): 1.13(d, 3H), 1.40–4.27(m, 14H), 6.00–7.57(m, 11H).
Elementary analysis as $C_{21}H_{28}N_2O_3$ (%):

|  | C | H | N |
|---|---|---|---|
| Calculated: | 70.76 | 7.92 | 7.86 |
| Found: | 70.51 | 8.00 | 8.11 |

EXAMPLES 28–32

Preparation of Compounds 16, 20, 22, 30 and 34

Compounds 16, 20, 22, 30 and 34 are obtained by repeating the same procedures as in Example 27 except using the compounds shown in Table 11 instead of Compound 14.

In Example 29, the free base is dissolved in a solvent and fumaric acid is added thereto, whereby Compound 20 is obtained as the fumarate.

TABLE 11

| Example | Compound number | Starting material/g | Yield (g) | Yield (%) |
|---|---|---|---|---|
| 28 | 16 | Compound 15/6.2 | 4.3 | 72 |
| 29 | 20 | Compound 19/4.5 | 1.0 | 21 |
| 30 | 22 | Compound 21/3.2 | 1.1 | 37 |
| 31 | 30 | Compound 26/1.5 | 0.3 | 21 |
| 32 | 34 | Compound 32/2.9 | 1.4 | 52 |

The properties of each compound are shown below.

Compound 16

1-(2-carbamoylphenoxy)-3-(1-methyl-3-phenyl-propylamino)-2-propanol.

Melting point: 111°–113° C.

Infra-red absorpion spectrum (KBr tablet, cm$^{-1}$): 3390, 3170, 1640, 1455, 1280, 1240.

N.M.R. spectrum (CDCL$_3$+d$_6$-DMSO, δ, p.p.m.): 1.07(d, 3H), 1.32–4.30(m, 12H), 6.63–8.13(m, 11H).

Elementary analysis as C$_{20}$H$_{26}$N$_2$O$_3$ (%):

|  | C | H | N |
|---|---|---|---|
| Calculated: | 70.15 | 7.65 | 8.18 |
| Found: | 70.37 | 7.79 | 7.95 |

Compound 20

1-(3-carbamoylmethylphenoxy)-3-(1-methyl-3-phenylpropylamino)-2-propanol fumarate.

Melting point: 83°–87° C.

Infra-red absorption spectrum (KBr tablet, cm$^{-1}$): 2930, 1660, 1600, 1410, 1260, 1160.

N.M.R. spectrum (measured as free base, CDCl$_3$, δ, p.p.m.): 1.13(d, 3H), 1.51–4.30(m, 14H), 5.83–7.53(m, 11H).

Elementary analysis as C$_{23}$H$_{30}$N$_2$O$_5$ (%):

|  | C | H | N |
|---|---|---|---|
| Calculated: | 66.65 | 7.30 | 6.76 |
| Found: | 66.28 | 7.26 | 6.61 |

Compound 22

1-(4-carbamoylmethylphenyl)-2-(1-methyl-3-phenyl-propylamino) ethanol.

Melting point: 156°–160° C.

Infra-red absorption spectrum (KBr tablet, cm$^{-1}$): 3360, 3180, 2920, 1635, 1415, 1070.

N.M.R. spectrum (d$_6$-DMSO, δ, p.p.m.): 1.02(d, 3H), 3.33(s, 2H), 1.37–4.70(m, 12H), 7.13(s, 4H), 7.19(s, 5H)

Elementary analysis as C$_{20}$H$_{26}$N$_2$O$_2$ (%):

|  | C | H | N |
|---|---|---|---|
| Calculated: | 73.59 | 8.03 | 8.58 |
| Found: | 73.41 | 7.78 | 8.32 |

Compound 30

1-(4-carbamoylmethylphenoxy)-3-{β-[N-benzyl-N-(1-methyl-2-phenoxyethyl)]} amino-2-propanol.

This compound is obtained as an oily free base.

Infra-red absorption spectrum (NaCl cell, cm$^{-1}$): 2910, 1660, 1600, 1510, 1240, 1035.

N.M.R. spectrum (d$_6$-DMSO, δ, p.p.m.): 1.12(d, 3H), 2.33–4.27(m, 18H), 6.00–7.50(m, 16H).

Elementary analysis as C$_{29}$H$_{37}$N$_3$O$_4$ (%):

|  | C | H | N |
|---|---|---|---|
| Calculated: | 70.85 | 7.59 | 8.55 |
| Found: | 71.02 | 7.77 | 8.29 |

Compound 34

1-(4-carbamoylmethylphenoxy)-3-{1-methyl-2-(4-methoxyphenoxy) ethylamino}-2-propanol.

Melting point: 140°–143° C.

Infra-red absorption spectrum (KBr tablet, cm$^{-1}$): 3490, 1685, 1515, 1250, 1035, 830.

N.M.R. spectrum (CDCl$_3$+d$_6$-DMSO, δ, p.p.m.): 1.12(d, 3H), 3.71(s, 3H), 2.38–4.05(m, 14H), 6.62–7.27(m, 8H).

Elementary analysis as C$_{21}$H$_{28}$N$_2$O$_5$ (%):

|  | C | H | N |
|---|---|---|---|
| Calculated: | 64.93 | 7.26 | 7.21 |
| Found: | 64.88 | 7.29 | 7.01 |

EXAMPLE 33

Preparation of Compound 17

In this example, 3 g of 1-(4-ethoxycarbonylmethyl-phenoxy)-3-(1-methyl-3-phenylpropylamino)-2-propanol (Compound 14) is dissolved in 20 ml of ethanol and then 20 ml of concentrated hydrochloric acid is added thereto. The mixture is heated under reflux for 3 hours. The solvent is then distilled away from the reaction solution under reduced pressure, and the residue is recrystallized from tetrahydrofuran-ether to obtain 1.5 g of 1-(4-carboxymethylphenoxy)-3-(1-methyl-3-phenylpropylamino)-2-propanol hydrochloride. (Yield: 49%).

Melting point: 160°–164° C.

Infra-red absorption spectrum (KBr tablet, cm$^{-1}$): 2930, 1700, 1300, 1240, 1180, 1050.

N.M.R. spectrum (CDCl$_3$+d$_6$-DMSO, δ, p.p.m.): 1.45(d, 3H), 3,48(s, 2H), 1.68–4.68(m, 11H), 6.60–7.47(m, 9H), 9.10(broad, 2H).

Elementary analysis as C$_{21}$H$_{28}$NO$_4$Cl (%):

|  | C | H | N |
|---|---|---|---|
| Calculated: | 64.03 | 7.16 | 3.56 |
| Found: | 63.79 | 6.99 | 3.52 |

EXAMPLE 34

Preparation of Compound 18

In this example, 4 g of 1-(4-ethoxycarbonylmethyl-phenoxy)-3-(1-methyl-3-phenylpropylamino)-2-propanol (Compound 14) is dissolved in 30 ml of ethanol and 6.1 g of 85% hydrazine hydrate is added thereto. The mixture is heated under reflux for 2 hours. The solvent is distilled away from the reaction solution under reduced pressure. The residue is recrystallized from tetrahydrofuran-ether to obtain 1.6 g of 1-(4-hydrazinocarbonylmethylphenoxy) -3-(1-methyl-3-phenylpropylamino)-2-propanol. (Yield: 42%), Melting point: 101°–105° C.

Infra-red absorption spectrum (KBr tablet, cm$^{-1}$): 2920, 1645, 1615, 1510, 1245, 1015.

N.M.R. spectrum (CDCl$_3$+d$_6$- DMSO, δ, p.p.m.): 1.10(d, 3H), 3.37(s, 2H), 1.37–4.20(m, 14H), 6.67–7.43(m, 9H), 8.87(s, 1H).

Elementary analysis as C$_{21}$H$_{29}$N$_3$O$_3$ (%):

|  | C | H | N |
|---|---|---|---|
| Calculated: | 67.90 | 7.87 | 11.31 |
| Found: | 68.01 | 7.88 | 11.23 |

REFERENCE EXAMPLE 1

Preparation of Compound EP-11

In this Reference Example, 18.0 g of ethyl m-hydroxyphenylethylacetate is dissolved in 150 ml of methylisobutylketone and then 10.2 g of sodium ethylate (powder) and 27.8 g of epichlorohydrin are added thereto. The mixture is heated under reflux for 3 hours. The reaction solution is then concentrated under reduced pressure and 200 ml of water is added thereto. The mixture is extracted twice with 150 ml of ether. The extract is dehydrated and concentrated under reduced pressure. The concentrate is distilled to obtain 17.7 g of ethyl m-(2,3-epoxypropoxy) phenylacetate (boiling point: 140°-142° C./0.3 mm Hg). (Yield: 75%).

REFERENCE EXAMPLE 2

Preparation of Compound AM-6

In this Reference Example, 50.0 g of p-acetonyloxyanisole is dissolved in 200 ml of ether and 60.0 g of benzylamine and 30 g of anhydrous magnesium sulfate are added thereto.

The mixture is allowed to stand overnight at room temperature. The magnesium sulfate is filtered off from the solution and the filtrate is concentrated under reduced pressure. The resulting residue is dissolved in 200 ml of ethanol and 7.6 g of sodium borohydride is added thereto under ice-cooling. The mixture is allowed to stand overnight under ice-cooling.

The reaction solution is concentrated under reduced pressure and 500 ml of water is added to the residue. The mixture is extracted twice with 150 ml of ether. The extract is dehydrated and concentrated under reduced pressure. The concentrate is distilled to obtain 60.2 g of N-benzyl-1-methyl-2-(4-methoxyphenoxy) ethylamine (boiling point: 175°-180° C./0.5 mm Hg). (Yield: 80.0%)

REFERENCE EXAMPLE 3

Preparation of Compound AM-7

In this Reference Example, 50 g of phenoxybenzamin hydrochloride is dissolved in 150 ml of water and the pH of the solution is adjusted to 11.0 with sodium hydroxide solution. The solution is extracted twice with 100 ml of chloroform.

Then, the extract is dehydrated and concentrated under reduced pressure. The residue is dissolved in 150 ml of DMF and 27.8 g of potassium phthalimide is added thereto. The mixture is heated with stirring for 3 hours at 110° C. DMF is distilled away from the solution under reduced pressure and 200 ml of water is added to the residue. The mixture is extracted twice with 150 ml of ether.

The extract is dehydrated and concentrated under reduced pressure. The residue is dissolved in 300 ml of ethanol and 9.4 g of 85% hydrazine hydrate is added thereto. The mixture is heated under reflux for 3 hours. The reaction solution is concentrated under reduced pressure and 300 ml of water is added thereto. Thereafter, the solution is made acidic with concentrated hydrochloric acid. The crystals deposited are filtered off from the solution and the pH of the filtrate is adjusted to 11.0 with sodium hydroxide solution. The solution is extracted twice with 200 ml of chloroform. Then, the extract is dehydrated and concentrated under reduced pressure to obtain 38 g of N-benzyl-N-(2-phenoxy-1-methylethyl) ethylenediamine as an oily substance. (Yield: 91%) (The obtained oily substance is pure enough to be used in the subsequent reaction without purification.) The oily substance is dissolved in ether and hydrogen chloride gas is bubbled thereinto to obtain the dihydrochloride as crystals. Melting point of this compound is 194°-198° C.

REFERENCE EXAMPLE 4

Preparation of Compound X-1

In this Reference Example, 14.8 g of 3-methyl-4-methoxypropiophenone is dissolved in 80 ml of acetic acid and 12.8 of bromine is added dropwise thereto at room temperature. The mixture is then stirred for 30 minutes at room temperature, whereby the color of bromine disappears. The acetic acid is distilled away from the solution under reduced pressure, and the resulting residue is washed with 100 ml of n-hexane to obtain 15.6 g of α-bromo-3-methyl-4-methoxpropiophenone as crystals. (Yield: 76%. Melting point of the desired compound recrystallized from carbon tetrachloride is 83°-86° C.

REFERENCE EXAMPLE 5

Preparation of Compound X-2

In this Reference Example, 38.4 g of 5-fluoro-3-methyl-2-acetylbenzo [b] furan is dissolved in 200 ml of acetic acid and 32.0 g of bromine is added dropwise thereto at room temperature. The mixture solution is then stirred for 30 minutes at room temperature, whereby the color of bromine disappears and crystals are deposited from the solution. Then, the solution is filtered to obtain 38.0 g of 5-fluoro-3-methyl-2-(α-bromoacetyl) benzo [b] furan as crystals. (Yield: 70%). Melting point of the desired compound recrystallized from ethanol is 120°-123° C.

What is claimed is:

1. A compound of the formula

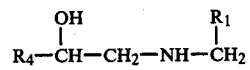

wherein $R_1$ represents

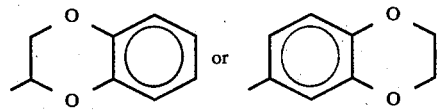

and $R_4$ represents

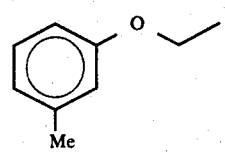

-continued

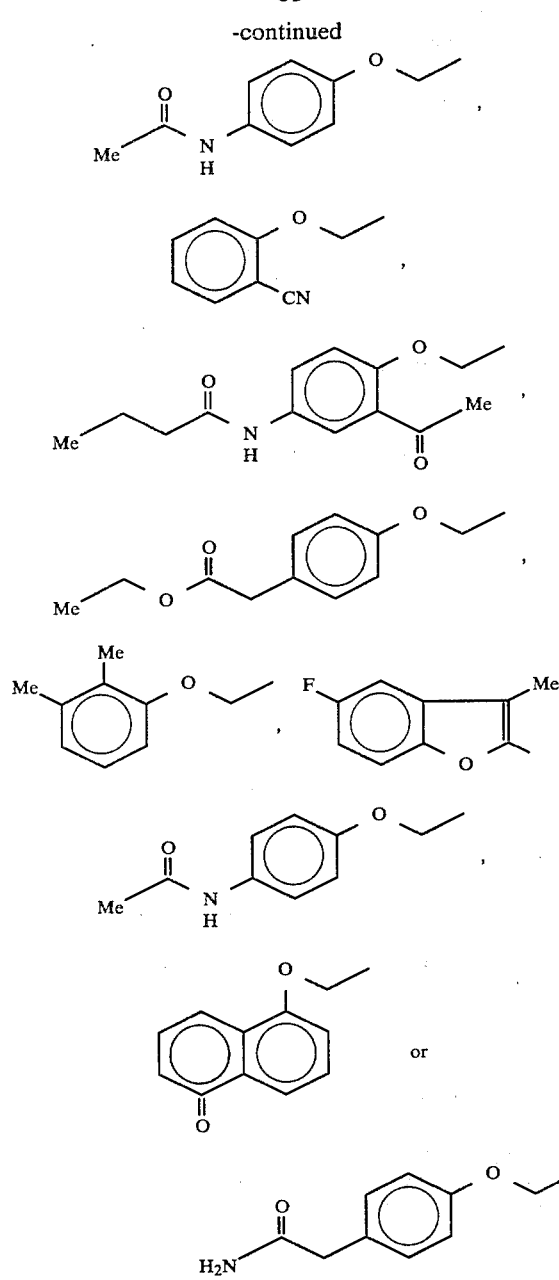

wherein Me represents a methyl group, and the pharmaceutically acceptable acid addition salts thereof.

2. A compound according to claim 1 of the formula

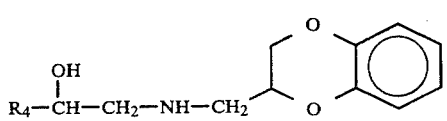

wherein R₄ represents

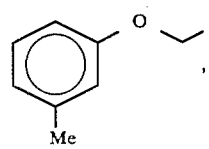

-continued

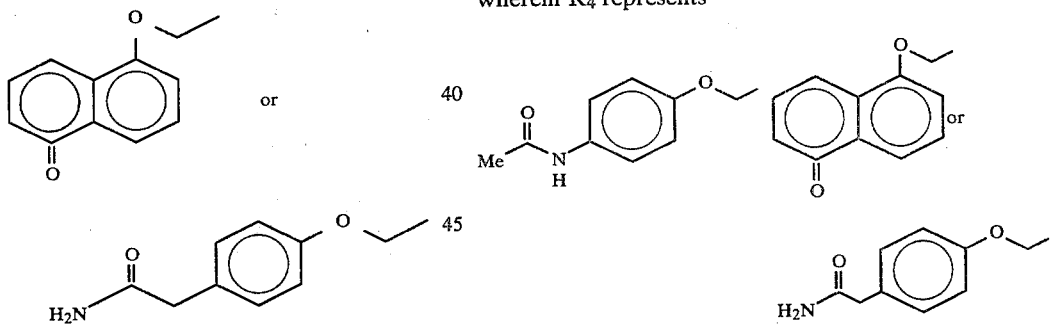

wherein Me represents a methyl group.

3. A compound according to claim 1 of the formula

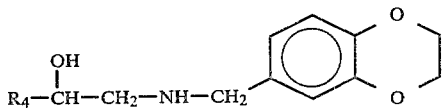

wherein R₄ represents

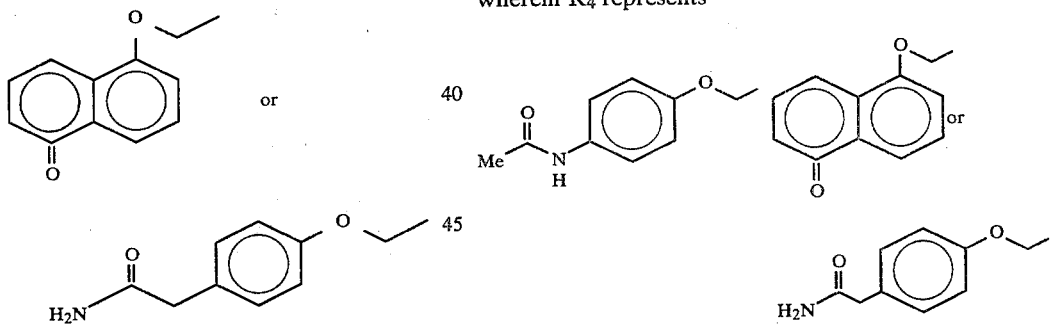

wherein Me represents a methyl group.

4. 1-(3-methylphenoxy)-3-(1,4-benzodioxane-2-methaneamino)-2-propanol.
 5. 1-(4-acetamidophenoxy)-3-(1,4-benzodioxane-2-methaneamino)-2-propanol.
 6. 1-(2-cyanophenoxy)-3-(1,4-benzodioxane-2-methaneamino)-2-propanol.
 7. 1-(4-butyrylamido-2-acetyl)phenoxy-3-(1,4-benzodioxane-2-methaneamino)-2-propanol.
 8. 1-(4-ethoxycarbonylmethyl)phenoxy-3-(1,4-benzodioxane-2-methaneamino)-2-propanol.
 9. 1-(2,3-dimethylphenoxy)-3-(1,4-benzodioxane-2-methaneamino)-2-propanol.
 10. 1-(5-fluoro-3-methyl-2-benzofuranyl)-2-(1,4-benzodioxane-2-methaneamino) ethanol.
 11. 1-(4-acetamidophenoxy)-3-(1,4-benzodioxane-6-methaneamino)-2-propanol.
 12. 1-{3,4-dihydro-1(2H)-naphthalenon-5-yl}oxy-3-(1,4-benzodioxane-6-methaneamino)-2-propanol.
 13. 1-(4-carbamoylmethylphenoxy)-3-(1,4-benzodioxane-6-methaneamino)-2-propanol.

* * * * *

UNITED STATES PATENT AND TRADEMARK OFFICE
CERTIFICATE OF CORRECTION

PATENT NO. : 4,381,398  
DATED : April 26, 1983  
INVENTOR(S) : HIROSHI TAKIZAWA, et al.

Page 1 of 3

It is certified that error appears in the above-identified patent and that said Letters Patent is hereby corrected as shown below:

Col. 6, line 10, the formula should read

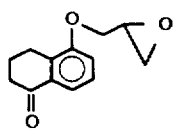

Col. 13, lines 1 - 10, insert the formula

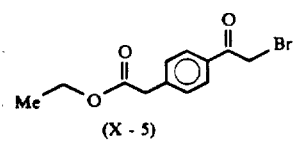

Col. 14, lines 1 - 10, delete the formula

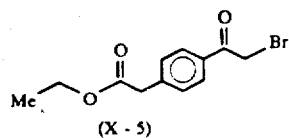

Col. 19, that portion of the structural formula for compound 24 reading

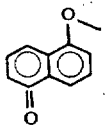

should read

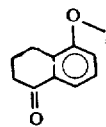

UNITED STATES PATENT AND TRADEMARK OFFICE
CERTIFICATE OF CORRECTION

PATENT NO. : 4,381,398

DATED : April 26, 1983

INVENTOR(S) : HIROSHI TAKIZAWA, et al.

It is certified that error appears in the above-identified patent and that said Letters Patent is hereby corrected as shown below:

Col. 20, adjacent the formula for compound 24, under the heading "$R_4$", the formula should be

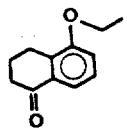

Col. 31, line 49, "butyrylaminodiphenoxy" should be -- butyrylamidophenoxy --.

Col. 39, line 40, the formula should be

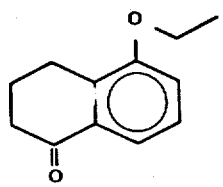

UNITED STATES PATENT AND TRADEMARK OFFICE
CERTIFICATE OF CORRECTION

PATENT NO. : 4,381,398

DATED : April 26, 1983

INVENTOR(S) : HIROSHI TAKIZAWA, et al.

It is certified that error appears in the above-identified patent and that said Letters Patent is hereby corrected as shown below:

Col. 40, line 40, the formula reading

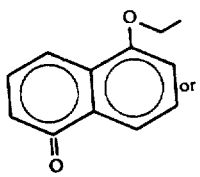

should read

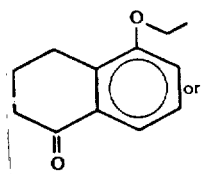

Signed and Sealed this

Thirteenth Day of September 1983

[SEAL]

Attest:

Attesting Officer

GERALD J. MOSSINGHOFF

Commissioner of Patents and Trademarks